(12) United States Patent
Bailey

(10) Patent No.: US 6,419,911 B1
(45) Date of Patent: Jul. 16, 2002

(54) PSYLLIUM CONTAINING SNACK BARS, PROCESSES FOR MAKING THESE, AND USES THEREOF

(75) Inventor: John Bailey, Battle Creek, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 08/123,557

(22) Filed: Sep. 17, 1993

(51) Int. Cl.[7] ............ A61K 7/06; A61K 47/00; A61K 35/37; A01N 43/04
(52) U.S. Cl. .............. 424/70.13; 424/439; 424/550; 424/551; 514/53; 514/57; 426/93; 426/629; 426/648; 426/658
(58) Field of Search ............ 424/195.1, 70.13, 424/439, 550, 551; 514/53, 57; 426/93, 104, 629, 648, 658

(56) References Cited

U.S. PATENT DOCUMENTS

| | | | |
|---|---|---|---|
| 3,574,634 A | 4/1971 | Singer | 99/83 |
| 4,348,379 A | 9/1982 | Kowalsky et al. | 424/34 |
| 4,565,702 A * | 1/1986 | Morley et al. | 426/93 |
| 4,619,831 A * | 10/1986 | Sharma | 426/93 |
| 4,766,004 A | 8/1988 | Moskowitz | 426/658 |
| 4,849,222 A | 7/1989 | Broaddus | 424/195 |
| 4,877,627 A * | 10/1989 | Leitz et al. | 426/285 |
| 4,950,140 A | 8/1990 | Pflaumer et al. | 424/439 |
| 5,009,916 A * | 4/1991 | Colliopoulos | 426/615 |
| 5,015,486 A | 5/1991 | Franssell et al. | 426/243 |
| 5,024,996 A | 6/1991 | Ringe et al. | 514/54 |
| 5,026,689 A | 6/1991 | Ringe et al. | 514/57 |
| 5,095,008 A | 3/1992 | Pflaumer et al. | 514/23 |
| 5,143,728 A | 9/1992 | Cappel et al. | 424/195 |
| 5,176,936 A * | 1/1993 | Creigton et al. | 426/618 |
| 5,223,298 A | 6/1993 | Wullschleger | 426/549 |
| 5,227,248 A | 7/1993 | Wullschleger | 426/549 |

* cited by examiner

Primary Examiner—Louise N. Leary
(74) Attorney, Agent, or Firm—Howard & Howard

(57) ABSTRACT

The invention is a psyllium containing snack bar. Also included as part of the invention are processes for making snack bars. The product may be used in a therapeutic or dietary regime, for purposes such as increasing dietary fiber or for reducing cholesterol. Dry mixes for making psyllium containing snack bars are also a feature of the invention.

17 Claims, No Drawings

PSYLLIUM CONTAINING SNACK BARS, PROCESSES FOR MAKING THESE, AND USES THEREOF

FIELD OF THE INVENTION

This invention relates to snack bar food products. More particularly, it relates to snack bars containing psyllium, as well as mixes useful in making the snack bars. The psyllium may be incorporated into the snack bars in any of a number of ways, so as to yield an organoleptically acceptable product. The snack bars may be used to assimilate psyllium into the diet for any of the therapeutic goals associated therewith.

BACKGROUND AND PRIOR ART

Psyllium is a known mucilaginous material which has found extensive use in bulk laxatives. The source of psyllium is seeds from the plants of the Plantago genus, which grow in certain sub-tropical regions. The seeds are dark brown, smooth, boat-shaped and shiny. Since it is believed by those skilled in the art that the active ingredient of psyllium is the psyllium seed gum, which is located primarily in the seed husk, present technology uses the ground seed husk as the source for psyllium. However, the whole seed is also known as a psyllium source, as well as the dehusked psyllium seed.

Due to the mucilaginous nature of psyllium, however, psyllium acquires a slimy or adhesive texture and mouthfeel upon hydration. This slimy mouthfeel is unpalatable and, accordingly, various additives have been incorporated in psyllium-containing ingestible compositions in order to mask the undesirable texture and mouthfeel of the psyllium. In addition, psyllium develops a distinctive, undesirable flavor in the presence of heat and moisture which further limits its use in food products.

Notwithstanding the undesirable flavor and texture imparted to an ingestible composition by psyllium or psyllium husks, various psyllium-containing foodstuffs have been proposed which purport to take advantage of the natural digestion regulation properties of psyllium, or the satiating or "fullness-feeling" effect of psyllium. See, for example, U.S. Pat. Nos. 3,574,634 and 4,348,379.

In addition, it has been suggested, for example, in U.S. Pat. No. 3,148,114, the whole psyllium husks, such as the ground husks of the seed of Plantago psyllium, lower blood cholesterol upon oral administration thereof. Further, it has also long been known to use small quantities of psyllium, such as less than 1%, as a thickener in foodstuffs, such as in ice cream, puddings and the like.

Finally, U.S. Pat. No. 4,849,222 discloses a medicament composition for reducing blood cholesterol levels in humans and lower animals which comprises a mixture of psyllium seed gum, or source of psyllium seed gum, and a nonabsorbable, nondigestible polyol polyester.

However, as set forth above, the mucilaginous nature of psyllium husks presents grave processing difficulties, and prior attempts to produce a palatable, ready-to-eat food product containing psyllium have not resulted in a satisfactory product to date, particularly, with respect to flavor and texture or mouthfeel.

Attempts have been made to incorporate psyllium into foodstuffs, so that the fiber can be consumed as part of a regular meal or other aspect of a normal diet, without any connotation or association with medicines, as well as with acceptable organoleptic properties. Examples of the patent literature involving psyllium incorporated into foodstuffs are U.S. Pat. Nos. 5,223,298 and 5,227,248, both of which are incorporated by reference. These patents teach psyllium containing ready to eat cereals. Additional examples of cereals containing psyllium are set forth by Moskowitz, U.S. Pat. No. 4,766,004; Ringe U.S. Pat. No. 5,024,996; and Ringe et al., U.S. Pat. No. 5,026,689. Other foodstuffs which include psyllium are taught in U.S. Pat. Nos. 5,095,008 and 4,950,140 both of which teach cookies with incorporated psyllium, and U.S. Pat. No. 5,015,486, which teaches microwavable muffins, U.S. Pat. No. 4,950,140 to Pflaumer et al. teaches the incorporation of psyllium into cookies, in order to treat gastrointestinal disorders and to reduce cholesterol. In applications Ser. Nos. 08/123,352, 08/123,353 and 08/123,342 concurrently filed and assigned to the assignee of the subject application, new food products containing psyllium are taught, including cereal, bread, and pasta. These disclosures are incorporated by reference in their entirety.

The manner in which food products such as cereal, bread and pasta are made are not appropriate for the manufacture of snack bars. As such, the invention also concerns processes for making the snack bars of the invention.

All features of the invention will be explained in the disclosure which follows.

DETAILED DESCRIPTION OF PREFERRED EMBODIMENTS

The following examples set forth preferred ways for making the snack bars of the invention. The formulation ranges for the finished products which constitute the invention are presented following the examples.

EXAMPLE 1

A fruit filled, psyllium containing snack bar was prepared.

To make the snack bars, the following ingredients were used:

| | |
|---|---|
| Shortening | 9.41 lb |
| Lecithin | 0.19 lb |
| Light Brown Sugar | 2.25 lb |
| Rolled Oats | 10.88 lb |
| Granulated Sugar | 9.00 lb |
| Vanilla | 0.23 lb |
| Ice Water | 10.28 lb |
| Na Al phosphate | 0.04 lb |
| Dough Salt | 0.56 lb |
| Hard Wheat Flour | 11.25 lb |
| Graham Flour | 12.00 lb |
| Baking Soda | 0.30 lb |
| Cinnamon | 0.15 lb |
| Extruded Psyllium (citric acid) | 8.25 lb |

The extruded psyllium was premixed with the shortening and 13 lb of water. This yielded a mixture which was incorporated into the snack bar at a later point in time, as indicated infra.

All other ingredients were combined in an industrial mixer, at low speed setting for three minutes. The mixing temperature was between 60 and 70° F.

After the dough ingredients were combined, the shortening/psyllium mixture was added thereto. The speed setting was the same, and the dough was mixed for one minute.

The psyllium containing dough was then co-extruded with a standard blueberry fruit filling, using an industrial co-extruder. This results in a product where the fruit filling is incorporated as a middle portion of the product.

The product of the coextrusion process described supra was cut into filled bars, which were baked for 7–8 minutes in a multizone oven. Specifically, an industry standard, multizone oven was used, wherein the bars were baked for about two minutes at 320° F., about two minutes at 450° F., about two minutes at 475° F., and then for a final period of about two minutes at 320° F. The final product resulted from this baking protocol.

Each bar weighed from about 44–49 grams, and contained about 39.5% by weight of blueberry filling. The product was deemed to have an acceptable texture and taste. The color was muddy brown or grayish, but this color could be changed via incorporation of any natural or artificial color into the mix.

EXAMPLE 2

The parameters of example 1 were followed, with one significant exception. In the second test, prewetted psyllium was used. Specifically, psyllium was combined with an equal amount of water prior to its use in the recipe.

The resulting product was organoleptically equivalent to the product of example 1 in all ways examined.

Prewetting the psyllium did not affect the snack bar in any noticeable way, although the prewetting step does facilitate the use of the psyllium.

The snack bars produced following examples 1 and 2 contained about 3.4 grams of psyllium per serving, defined herein as about 50 g of snack bar.

In the preparation of the snack bars of examples 1 and 2, water was added to the mixes as needed to produce a workable dough. Water was added, as appropriate, to form a suitable material for baking. The addition of water or other forms of moisture prior to baking is a standard technique. Firm guidelines as to amounts cannot be given, as factors which include, e.g., the batches from which dry materials are taken, temperature, humidity, and so forth, as well as the manner of preparing the dough impact on this. One of ordinaly skill in the art will recognize when a dough product is ready for baking. In any event, finished baked goods must conform to particular standards, such as moisture content. If, after a given time, the baked products contains excess moisture (a value which is easily obtained), the length of time and/or temperature of baking may be extended.

EXAMPLE 3

In the following example, a snack bar was prepared which did not use a filling. The following ingredients were used:

| Shortening | 9.75 lb |
| --- | --- |
| Psyllium Nuggets | 14.00 lb |
| Lecithin | 0.75 lb |
| Cinnamon | 1.28 lb |
| Granulated Sugar | 12.00 lb |
| Vanilla | 0.53 lb |
| Dough Salt | 0.23 lb |
| Sodium bicarbonate | 0.30 lb |
| Na Al phosphate | 0.15 lb |
| Dextrose | 3.75 lb |
| Flour | 18.48 lb |
| Rolled Oats | 5.25 lb |
| Water | 8.55 lb |

The psyllium and shortening were again preblended, as in example 1, although it must be understood that this is not necessary. The choice of whether or not to preblend the shortening and psyllium depends, for example, on whether coextrusion, rotary forming, or other manner or preparation are used. An example follows where there was no preblending, as proof of this. The remaining ingredients except water were combined, and mixed in the same way as the ingredients in the first example. Specifically, all of the listed ingredients except psyllium, shortening and water were combined in an industrial mixer at low speed, and mixed for three minutes at a temperature of from 60–70° F. Following this, the water was added, and mixed under the same conditions. Finally, the combination of shortening and psyllium was added, and combined for one minute at the recited conditions. Individual snack bars were rotary formed, and were then baked for 7–8 minutes in a multizone oven, at a temperature range of from about 200 to 500° F. This produces a flat, crispy snack bar product. These products were analyzed. A single serving, which weighed from about 30–40 grams, contained about 3.4 grams of psyllium, and about 2–4% moisture.

EXAMPLE 4

As indicated, supra this example describes preparation of a snack bar in accordance with the invention where preblending of shortening and psyllium is not employed.

The following ingredients were used:

| Shortening | 9.75 lb |
| --- | --- |
| Lecithin | .75 lb |
| granulated sugar | 10.88 lb |
| granulated salt | .23 lb |
| ground cinnamon | 1.28 lb |
| vanilla extract | .76 lb |
| dextrose | 3.75 lb |

These ingredients were creamed in an industrial blender for two minutes, at low speed. Following the creaming step, 5.50 lbs of water were added and mixed for one minute at low speed.

The moistened material was then combined with the following:

| White flour | 13.75 lb |
| --- | --- |
| Rolled Oats | 4.25 lb |
| sodium bicarbonate | .30 lb |
| sodium aluminum phosphate | .15 lb |
| psyllium nuggets | 21.00 lb |

These dry ingredients were combined with the wet ingredients at low blender speed, for four minutes.

The dough was baked in the manner described supra. The formulation produced an acceptable snack bar with 35% moisture, and free of cracks. A 25 gram serving contained 3.4 grams of psyllium.

EXAMPLE 5

The cholesterol lowering effect of the psyllium enriched snack bars of this invention is confirmed by the following study.

Over the course of six months, a long term intervention study is conducted to test the effect of the psyllium enriched product on the level of serum cholesterol on sample size of 250 hypercholesterolemic individuals. Individuals chosen for this study are at risk for mild abnormalities in their cholesterol levels. Generally, the study targets individuals with plasma LDL-cholesterol levels at 130 to 220 mg/dl, with the proviso that their triglycerides levels are less than 300 mg/dl. There is an initial eight week dietary instruction and stabilization period where lipid criteria are ascertained.

According to the protocol of the intervention study, the individuals participating in the study are divided into four groups. The groups are administered varying number of servings of a psyllium enriched food product to determine whether there is a dose dependent hypocholesterolemic effect. The participants are given a choice of psyllium enriched food products: R-T-E-cereal, bread, snack bars, and pasta, which are packaged in zero and 3 mg psyllium servings. All products are prepared in accordance with the copending applications cited supra.

Group A is given three servings of the placebo product per day and is not administered a psyllium food product at all.

Group B is given two servings of the test product and one serving of the placebo product per day.

Group C is given one serving of the test product and two servings of the placebo product per day.

Group D is given three servings of the test product per day and no placebo.

The serum cholesterol levels are tested periodically during the study by taking blood samples and determining cholesterol level in the serum.

The cholesterol levels decrease from baseline over the course of the study indicating the hypocholesterolemic effect of psyllium enriched products. The study further shows that the decrease in serum cholesterol is in proportion to the dosage units of psyllium product ingested.

The foregoing examples describe the manufacture of snack bars containing psyllium. Two different types of product are produced. In example 1, a soft, chewy type of product results, whereas the snack bar of example 3 is a crisper, crunchier material. The differences in texture result, inter alia, from differences in moisture content, as elaborated upon infra.

As will be noted, psyllium is an essential ingredient of the snack bars of the invention. The doughs used to prepare the snack bars are formulated such that the finished product will preferably contain from about 2.0 g to about 4.0 g of psyllium per 35 g serving. It must be noted that a "serving" may be more than 35 g, as the softer bars of the invention will weigh more than the crispier bars. In any event, the finished product, i.e., the snack bar, should contain anywhere from about 1% to about 20% by weight of psyllium. In a preferred embodiment, the finished product contains from about 2% to about 12% by weight psyllium. The psyllium may be obtained from any of the raw materials known to the art as being a source of psyllium, including unprocessed or raw psyllium, prewetted psyllium, psyllium nuggets, ground psyllium powder, encapsulated psyllium and so forth. Psyllium nuggets may be prepared in accordance with U.S. Pat. Nos. 5,223,298 and 5,227,244, the disclosures of which is incorporated by reference.

The moisture content of the psyllium containing snack bar may vary, it being especially preferred that the snack bar containing anywhere from about 2% to about 20% by weight of moisture. At moisture contents above about 20%, it is difficult to store the snack bars, due to spoilage problems, although values higher than 20% may be secured when the product is made "at home", as discussed infra.

Of course, the higher the moisture content, the softer and chewier the snack bar product will be. Within the preferred range of from 2–20% moisture, softer products more preferably contain from about 10% to about 20% moisture, and most preferably from about 12% to about 16% moisture. If a crispier product is desired, it preferably contains from about 2% to about 10% moisture, and most preferably from about 2% to about 5% moisture.

The snack bars of the invention require, as additional components, shortening, a sweetener and a grain product. "Shortening" as used herein, refers to any edible fat or fat substitute which is stable during baking. Included therein are vegetable shortenings, edible oils such as corn oil, cottonseed oil, rapeseed oil, palm oil, coconut oil, and so forth, liquid and solid soy oil products, oleomargarine, margarine, and so forth. The shortening may also be comprised, in whole or in part, of fat substitutes such as olestra. The finished product contains from about 10% to about 20% by weight of shortening.

"Sweetener" includes all natural and synthetic materials used as sweetening agents, including white sugar, cane and beet sugar, dark and light brown sugar, honey, molasses syrups such as maple syrup and sorghum syrups, fruit syrups, fruit juice concentrates, "NUTRASWEET®", "SUCRALOSE®" and so forth.

The finished product, i.e., the snack bar, preferably contains from about 10% to about 20% by weight of the sweetener when a natural sweetener is used. The amount of sweetener can be reduced to from about 10% to about 15% by weight as well. If artificial sweeteners, such as NUTRASWEET® or sucralose are used, the total amount by weight can, and must be reduced, possibly to as little as 1% by weight. Thus up to about 20% by weight of the finished product may be a sweetener, the amount depending, inter alia, on the type of sweetener used.

"Grain product" encompasses any edible material obtained from any grain, including wheat, oats, corn, barley, rice, rye, and so forth. Flours, grits, bran, flaked materials, groats, meal, and so forth are included, as are processed materials derived from grains. Exemplary of these are ready-to-eat cereals such as puffed or crisped rice, cereal flakes such as cornflakes, toasted grains, etcetera.

The grain product is the major component of the finished product, and constitutes anywhere from about 40% to about 80% of the snack bar by weight. In a preferred embodiment, the finished snack bar contains from about 50% to about 80% of grain product, and may even contain from about 60% to about 80% by weight of grain product.

It was pointed out, supra, that the snack bars of the invention may contain more than 20% by weight of moisture if made at home. Indeed, a further aspect of the invention is a prepared mix useful for making psyllium containing snack bars at home, using standard ovens and/or microwave ovens, e.g. Such mixes do not contain added moisture or shortening oil, as these are added at home, but the dry mixes do contain the psyllium, the sweetener, and the grain product as described supra, over the recited ranges. of course, in the dry mixes of the invention, liquid sweeteners are not used; rather dried, powdered, or crystallized sweeteners are preferred. Where moist ingredients, such as the fruit fillings, and icings described infra are used, these are provided as a separate component of the mix. For example, a boxed dry mix may contain a separate, bagged portion of the dry ingredients, together with a can, tube, or other container of wet or moist ingredients and/or filling. Instructions will accompany the mixes, to facilitate preparation of a moist or crispy product.

The snack bars may also contain additional optional ingredients, such as ingredients based upon fruit, nuts, flavorings, spices, and vegetables. The blueberry filled snack bars produced in examples 1 and 2 are exemplary of snack bars containing fruit ingredients. Other fruits which may serve as the basis for the snack bar ingredient included strawberries, raspberries, apples, figs, dates, citrus fruits, dried fruits such as raisins and cranberries and so forth. These fruit ingredients may be in the form of a puree, a marmalade, a jam, a preserve, a candied peel, a dried fruit product, and so forth. The optional nut ingredient includes any type of nut, in whole, chopped, ground, grated or powdered form, as well as others not recited herein in view of their notoriety. The optional flavor ingredient includes essences and extracts such as vanilla, chocolate, almond, and all others used in the culinary arts. This is also true of the optional spice ingredient. The snack bars may also be frosted, coated or enrobed by materials such as chocolate, yogurt, and other standard coatings well known in the art. If desired, the snack bars may include fortifying ingredients such as vitamins, minerals, food supplements, and so forth.

The process by which these snack bars are made is also a feature of the invention. In one embodiment, the shortening and psyllium may be precombined before incorporation into the remaining ingredient, however, this is not required. In the first embodiment, psyllium and shortening are combined in a discrete step. The sweetener, grain product and water are combined, apart from psyllium and shortening. The two mixes are then combined, and baked to form a snack bar. In the second embodiment, shortening is added after the grain product, sweetener and moisture are combined. After this, the prewet psyllium is added, and the resulting mixture processed to form a snack bar.

"Snack bar" as used herein, refers to a baked product which has substantially less sugar and has substantially more grain product than a cookie. For example, U.S. Pat. No. 5,095,008 to Pflaumer et al describes conventional cookie dough as containing 20–50% by weight of sugar, and 4–25% by weight of flour, where a portion of the latter can be replaced by other products. The artisan of ordinary skill will immediately note that a dough, which by definition contains moisture, will yield a baked product containing substantially more than 20% sugar by weight if the dough contains this quantity of sugar. While the percent by weight of flour will also increase, it would not increase to, e.g., 40% by weight of the finished product.

In the manufacture of the products described herein, it will be understood that optional ingredients may be added at any time which is suitable for that ingredient. A coating, for example, is of course added at the very end of the processing. Flavor ingredients and spice ingredients are best added to the sweetener/grain moisture mixture. Fruit ingredients may be added either during the mixing and baking steps, or as a coextruded ingredient, as a middle, bottom or top layer in a baked product, etcetera.

The snack bars of the invention are useful in any of the ways psyllium has been used in the past. As indicated supra, psyllium has long been known as a source of increased dietary fiber. Similarly, it is now known as a cholesterol reducing agent. Thus, another aspect of the invention relates to a method for reducing cholesterol by consuming an amount of the inventive snack bars sufficient to provide a cholesterol lowering amount of psyllium to the subject. While the amount of psyllium necessary to accomplish this goal may vary, preferably between 10 and 25 grams of the psyllium should be consumed per day. The snack bars can be used to provide all of the psyllium, or they can be used in combination with other food sources of psyllium, including, but not limited to, cereal, (especially ready-to-eat cereal), bread, pasta, cookies, beverages, and so forth. Other food products may also be used, as will be recognized by the skilled artisan.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A psyllium containing baked snack bar which comprises, per snack bar:

from about 5.7% to about 20% by weight psyllium;

from about 10% to about 20% by weight shortening;

up to about 20% by weight sweetener;

from about 50% to about 80% by weight grain product, and;

from about 2% to about 20% by weight moisture.

2. The baked snack bar of claim 1, comprising from about 5.7% to about 12% by weight psyllium.

3. The snack bar of claim 1, comprising from about 10% to about 15% by weight sweetener.

4. The snack bar of claim 1, comprising from about 60% to about 80% by weight grain product.

5. The snack bar of claim 1, comprising from about 2% to about 10% by weight moisture.

6. The snack bar of claim 5, comprising from about 2% to about 5% by weight moisture.

7. The snack bar of claim 1, comprising from about 10% to about 20% moisture.

8. The snack bar of claim 7, comprising from about 12% to about 15% moisture.

9. The snack bar of claim 1, further comprising at least one additional ingredient selected from the group consisting of a fruit ingredient, a nut ingredient, a flavor ingredient, a spice ingredient, and a vegetable ingredient.

10. The snack bar of claim 1, wherein said grain product is a wheat based product.

11. The snack bar of claim 1, wherein said grain product is an oat-based product.

12. Method for reducing serum cholesterol in a subject in need thereof comprising administering to said subject a serum cholesterol lowering amount of the snack bar of claim 1.

13. The snack bar of claim 1, prepared by:

(a) blending said shortening and said psyllium to form a first mixture;

(b) combining said sweetener and said grain product with an amount of water sufficient to form a moistened, second mixture;

(c) combining said first and second mixture to form an uncooked snack bar product; and (d) baking said uncooked snack bar product.

14. Process for preparing a psyllium containing snack bar, comprising:

(i) mixing psyllium and shortening to form a first mixture, (ii) mixing a sweetener and a grain product with water to form a moistened second mixture, (iii) combining said first and second mixture to form a third mixture, and (iv) baking said third mixture to form a snack bar, wherein said third mixture comprises, on a weight percent basis:

(i) from about 1% to about 20% psyllium;
(ii) from about 5% to about 20% shortening;
(iii) up to about 20% sweetener;
(iv) from about 50% to about 70% grain product, and
(v) from about 10% to about 40% water.

15. Dry mix useful for preparing a psyllium containing snack bar, comprising:
(i) from about 1% to about 20% by weight psyllium;
(ii) up to about 20% by weight of a dry sweetener; and
(iii) from about 50% to about 80% by weight of a grain product.

16. The baked snack bar of claim 1, wherein said baked snack bar contains from about 2.0 g to about 4.0 g of psyllium per 35 g of baked snack bar.

17. The process of claim 14, wherein said baked snack bar contains from about 2.0 g to about 4.0 g of psyllium per 35 g of baked snack bar.

* * * * *